(12) United States Patent
Mohamadi

(10) Patent No.: US 12,178,933 B2
(45) Date of Patent: Dec. 31, 2024

(54) NEAR-FIELD NARROW-BAND MICROWAVE DEVICE FOR INACTIVATION OF VIRUS

(71) Applicant: Farrokh Mohamadi, Irvine, CA (US)

(72) Inventor: Farrokh Mohamadi, Irvine, CA (US)

(*) Notice: Subject to any disclaimer, the term of this patent is extended or adjusted under 35 U.S.C. 154(b) by 741 days.

(21) Appl. No.: 17/230,930

(22) Filed: Apr. 14, 2021

(65) Prior Publication Data

US 2022/0111099 A1 Apr. 14, 2022

Related U.S. Application Data

(60) Provisional application No. 63/089,496, filed on Oct. 8, 2020.

(51) Int. Cl.
*A61L 2/28* (2006.01)
*A61L 2/12* (2006.01)

(52) U.S. Cl.
CPC ...... *A61L 2/28* (2013.01); *A61L 2/12* (2013.01); *A61L 2202/11* (2013.01); *A61L 2202/122* (2013.01)

(58) Field of Classification Search
CPC .......... A61L 2/12; A61L 2/28; A61L 2202/11; A61L 2202/122
See application file for complete search history.

(56) References Cited

U.S. PATENT DOCUMENTS

2003/0070922 A1* 4/2003 Ishii ............... H01J 23/20
  204/298.19
2011/0014331 A1* 1/2011 Stull, Jr ............. H05B 6/6402
  426/241

OTHER PUBLICATIONS

Yang et al., "Efficient Structure Resonance Energy Transfer From Microwaves to Confined Acoustic Vibrations in Viruses", Scientific Reports, www.nature.com/scientificreports, Published on Dec. 9, 2015, 10 pages.
Desai et al., "Raman Spectroscopy Based Detection of RNA viruses in Saliva: a preliminary report", Journal of Biophotonics, dated Jul. 2020, 8 pages.

* cited by examiner

*Primary Examiner* — Sean E Conley
(74) *Attorney, Agent, or Firm* — Haynes and Boone, LLP

(57) ABSTRACT

A microwave device for inactivation of viruses is disclosed. The microwave device comprising a housing and a field generator. The housing has a cavity configured to receive an object contaminated with viruses within the cavity and the field generator is configured to irradiate the cavity with microwave energy at a band of frequencies and a power level configured to inactivate the virus. The cavity is located within a near-field of a radiation pattern produced by the field generator at the band of frequencies and the microwave energy causes a dipole vibration on the virus that causes the virus to fracture.

14 Claims, 5 Drawing Sheets

NEAR-FIELD NARROW-BAND MICROWAVE DEVICE FOR INACTIVATION OF VIRUS

CROSS-REFERENCE TO RELATED APPLICATIONS

This application claims the benefit of U.S. Provisional Application No. 63/089,496 filed Oct. 8, 2020, the contents of which are hereby incorporated by reference in their entirety.

TECHNICAL FIELD

This application relates generally to the sterilization of objects to inactivate viruses utilizing microwave energy.

BACKGROUND

At present, society has experienced numerous virial epidemics around the world that have spread from one side of the world to another. These virial epidemics have necessitated the need to sterilize aerosols ejected from talking or coughing to stop the spread of these virial epidemics and any future outbreaks. Specifically, in the past few decades, tremendous efforts have been made to kill airborne viruses such as severe acute respiratory syndrome (SARS) coronavirus or influenza viruses, which have caused catastrophic illness worldwide. Current techniques for airborne virus epidemic prevention used in public space includes the use of strong chemical inactivation, ultraviolet (UV) irradiation, and microwave thermal heating.

Unfortunately, all these methods adversely affect the open public and have drawbacks because strong chemicals are usually poisonous and/or carcinogenic, UV irradiation only effects the surface of an object and does not penetrate deep into the object, and microwave thermal heating techniques generally require high enough power to be dangerous to humans. As such, there is a need for an improved system and method for destroying virus that is safe to utilize.

SUMMARY

A microwave device for inactivation of viruses is disclosed. The microwave device comprising a housing and a field generator electromagnetics field generator. The housing has a cavity configured to receive an object having a virus within the cavity and the field generator is configured to irradiate the cavity with microwave energy at a band of frequencies and a power level configured to inactivate the virus. The cavity is located within a near-field of a radiation pattern produced by the field generator at the band of frequencies and the microwave energy causes a dipole vibration on the virus that causes the virus to fracture.

In an example of operation, the microwave device performs a method that includes placing an object with the virus within the cavity of the housing, generating a microwave signal with a microwave signal generator, and irradiating the cavity with a microwave energy generated by a field generator in response to receiving the microwave signal. In this example, the microwave signal is within the band of frequencies and the power level configured to inactivate the virus and the cavity is within a near-field of the field generator.

Other devices, apparatuses, systems, methods, features, and advantages of the invention will be or will become apparent to one with skill in the art upon examination of the following figures and detailed description. It is intended that all such additional devices, apparatuses, systems, methods, features, and advantages be included within this description, be within the scope of the invention, and be protected by the accompanying claims.

BRIEF DESCRIPTION OF THE DRAWINGS

The invention may be better understood by referring to the following figures. The components in the figures are not necessarily to scale, emphasis instead being placed upon illustrating the principles of the invention. In the figures, like reference numerals designate corresponding parts throughout the different views.

FIG. 1 is a system block diagram of an example of an implementation of a microwave device for inactivation of viruses in accordance with the present disclosure.

FIG. 2A is a side view of an example of an implementation of a combination of the housing and field generator helices wiring shown in FIG. 1 field in accordance with the present disclosure.

FIG. 2B is a cut-away side view of the combination of the housing and field generator shown in FIG. 2A in accordance with the present disclosure.

FIG. 2C is a top view of the combination of the housing and field generator shown in FIG. 2A in accordance with the present disclosure.

FIG. 3 is a top view of an example of an implementation of another combination of the housing and field generator shown in FIG. 1 in accordance with the present disclosure.

FIG. 4 is a flowchart of an example of an implementation of a method performed by the microwave device shown in FIG. 1 in accordance with the present disclosure.

FIG. 5 is a system flow diagram of an example of an implementation of the method described in FIG. 4 in accordance with the present disclosure.

DETAILED DESCRIPTION

In FIG. 1, a system block diagram is shown of an example of an implementation of a microwave device 100 for inactivation of viruses on an object 102 in accordance with the present disclosure. In this example, the microwave device 100 includes a housing 102 having a cavity 104 and a field generator 106. The cavity 104 is within a near-field 108 of the radiation pattern 110 of the field generator 106 and the field generator 106 is electrically connected to a microwave signal generator 112. As an example, the field generator 106 may be an antenna.

In an example of operation, the object 102 is placed within the cavity 104 and a microwave signal 114 is generated by the microwave signal generator 112 that is transmitted to the field generator 106. The field generator 106 receives the microwave signal 114 and irradiates the cavity 104 with microwave energy 116. In this example, the microwave energy 116 is chosen from a band of frequencies and the microwave energy that causes a dipole vibration on the virus that results in fracturing the virus.

In general, a virus is a submicroscopic infectious agent that replicates only inside the living cells of an organism. Viruses infect all types of life forms, from animals and plants to microorganisms, including bacteria and archaea. When infected, a host cell is forced to rapidly produce thousands of identical copies of the original virus. When not inside an infected cell or in the process of infecting a cell, viruses exist in the form of independent particles, or virions, consisting of: (i) the genetic material, i.e., long molecules of RNA that encode the structure of the proteins by which the virus acts; (ii) a protein coat, the capsid referred to as lipid layers, which surrounds and protects the genetic material Generally, a lipid layer is any of a class of organic compounds that include fatty acids or their derivatives and are insoluble in water but soluble in organic solvents. As an example, lipids include many natural oils, waxes, and steroids. Generally, lipids have dipolar molecules which can be excited into dipolar mode vibrations with a varying electromagnetic field. As such, in this disclosure, the process of inactivating (i.e., destroying) a virus is done by radiating a virus with electromagnetic energy within a certain band of frequencies, power levels, and dwelling time. This electromagnetic energy causes the water molecules of an aerosol droplet surrounding the lipids protecting a virus to vibrate in a dipolar mode based on the changing polarity of waveform of the electromagnetic energy. As the frequency of the electromagnetic energy changes so does the frequency of vibration of the dipolar water molecules in the lipids. Likewise, as the power level of the electromagnetic energy increases, so does the intensity of the dipolar mode vibrations. Moreover, the dwell time of the electromagnetic energy also keeps the water molecules vibrating to the point of failure within the lipid. As such, by varying the frequency, power level, and dwell time of the electromagnetic energy being directed towards a virus resting on a lipid, the microwave device disclosed herein can cause rupture of the lipid layer on which the virus in enclosed causing the destruction of the virus.

Figure 1:
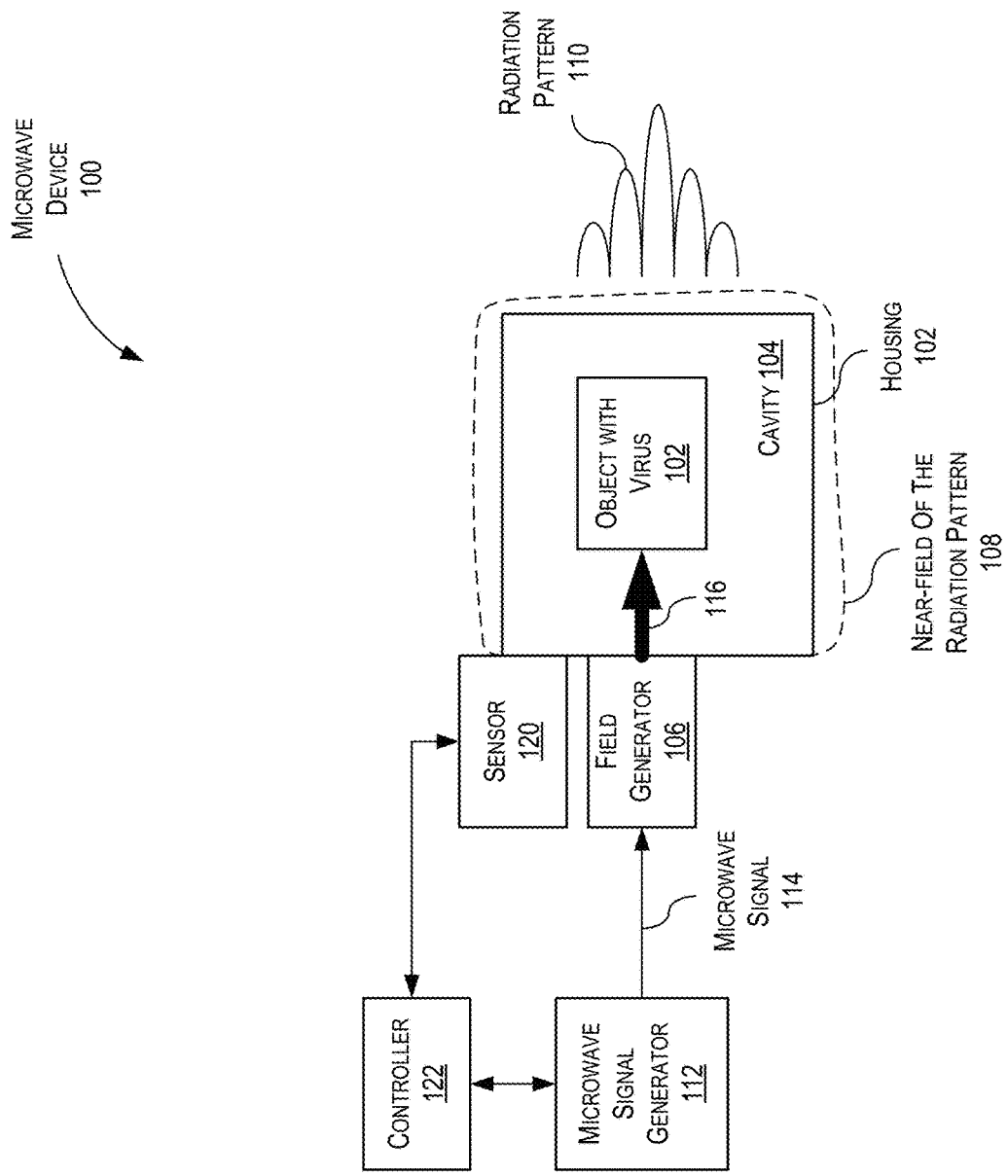

Turning back to FIG. 1, the microwave device 100 may also include a sensor 120 and controller 122. The controller 122 may be electrically connected to both the sensor 120 and microwave signal generator 112 and may be configured to control both devices. The sensor 120 may be any device capable of monitoring the presence and/or state of one of more viruses within the cavity 104 on the object 102. As such, the controller 122 is configured to determine whether a virus (or viruses) on the object 102 have been destroyed (i.e., inactivated) with the sensor 120. To destroy a virus in the cavity 102, the controller 122 controls the operation of the microwave signal generator 112 to change frequency of operation, power level, or dwell time.

In general, the microwave device 100 is designed to radiate the electromagnetic energy (herein referred to generally as "microwave energy 116") into the cavity 104 towards the virus on the object 102. In this disclosure, the microwave device 100 is designed such that the cavity 104 of the housing 102 is located within the near-field 108 of the radiation pattern 110 produced by the field generator 106. By being within the near-field 108 of the radiation pattern 110, the cavity 104 will be injected with multi-mode electromagnetic radiation that have numerous polarities and modes causing a chaotic intensity of dipolar vibration that is greater than a dipolar vibration caused by a more defined radiation field in the radiation pattern 110. The cavity is the conduit for the aerosol or objects be placed inside the electromagnetic field to be radiated effectively. In this example, varying types of field generator 106 may be utilized. Examples, include patch field generators, resonant cavity field generators, helical field generators, etc.

Figure 2B:
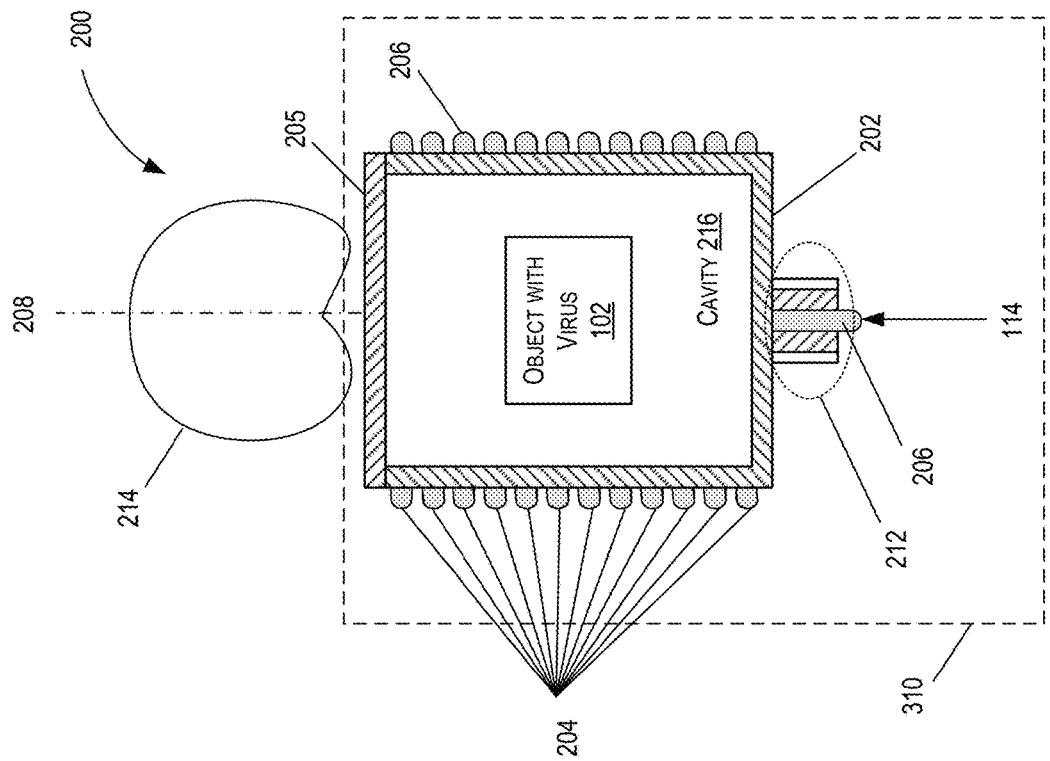
Figure 2A:
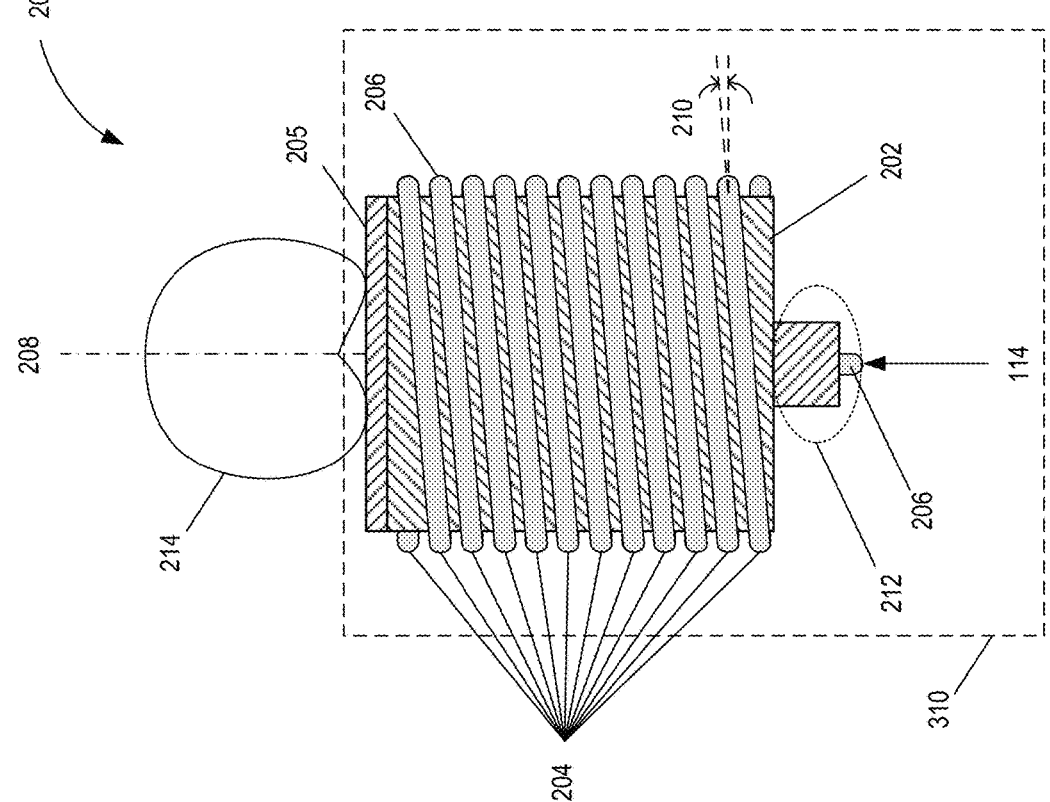

In FIG. 2A, a side view of an example of an implementation of a combination 200 of a housing 202 and helical field generator 204 is shown in accordance with the present disclosure. The housing 202 may include a removable top 205, a cavity to pass through the aerosol in a plastic tube, and fixate the placement of conductor rings and plates such as, for example, a metallic wire 206 wrapped around the housing 202.

In this example, the metallic wire 206 may be a copper wire. As an example of an implementation, the copper wire may be one millimeter copper wire that has an approximate length of 126 centimeters to form the helical pattern of the copper wire 206 wrapping around the housing 202 may be approximately 4.5 centimeters height. For an electromagnetic wave to fire along the boresight 208 of the helical field generator 204 without significant lateral radiation along directions away for the boresight 208, the copper wire 206 should have a slope 210 that is approximately equal to the arcsine of a height of the helical pattern divided a length of the metallic wire. In this specific example, the slope angle would be approximately 2 degrees. The assembly is placed in a shielded metallic cylinder 310 that is attached to the Ground layer.

Moreover, in this example, the housing 202 may have a radio frequency (RF) connector 212 electrically connected to a bottom of the housing 202 and the copper wire 206. The RF connector 212 may be a subminiature version A (SMA) connector that is electrically connected to the microwave generator 112 and is configured to receive the microwave signal 114.

In an example of operation, the combination 200 of the housing 202 and the helical field generator 204 is configured to receive the microwave signal 114 and produce a radiation pattern 214 that is fired in the direction of the boresight 208. In these examples, the housing 202 may constructed of a low-dielectric material such as, for example, a TEFLON® type material, synthetic resin such polytetrafluoroethylene. The housing 202 may also be cylindrical or cubic in shape. Based on the example previously described the housing 202 may be cylindrical having a height approximately equal to 4.5 centimeters and a diameter of approximately equal 4 centimeters.

Figure 2C:
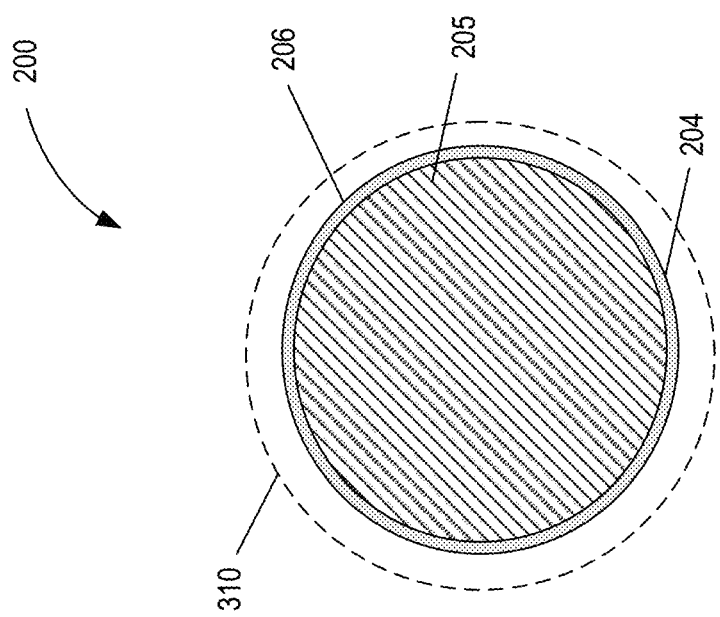

FIG. 2B is a cut-away side view of the combination of the housing and field generator 200 in accordance with the present disclosure. In this example, the object 102 with a virus is shown within the cavity 216 within the housing 202. In FIG. 2C, a top view of the combination 200 of the housing and field generator is shown in accordance with the present disclosure.

Figure 3:
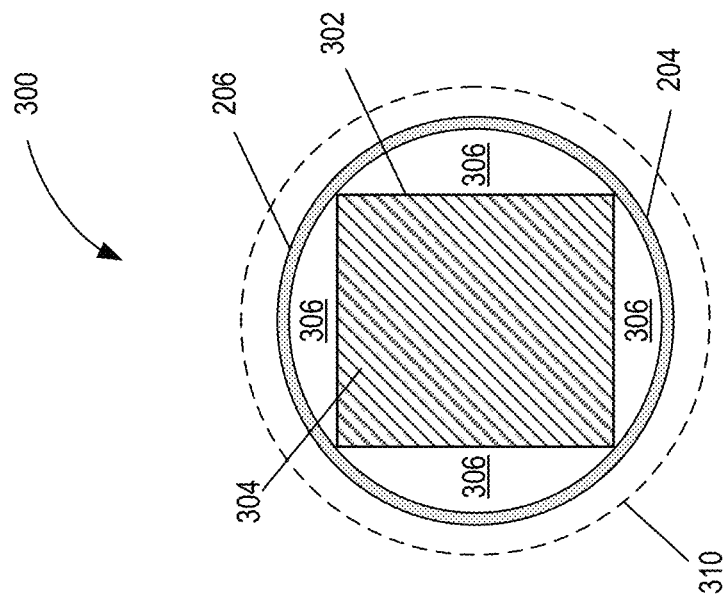

Turning to FIG. 3, a top view of an example of an implementation of another combination 300 of the housing and field generator is shown in accordance with the present disclosure. In this example, the housing 302 and removable top 304 may be cylindrical or cubical in shape such that other dielectric and/or air may fill the space 306 between the housing 302 and the copper wire 206 forming the helical field generator 204.

In all of these examples, the band of frequencies may be the X-band that extends from 6 GHz to 12 GHz.

Figure 4:
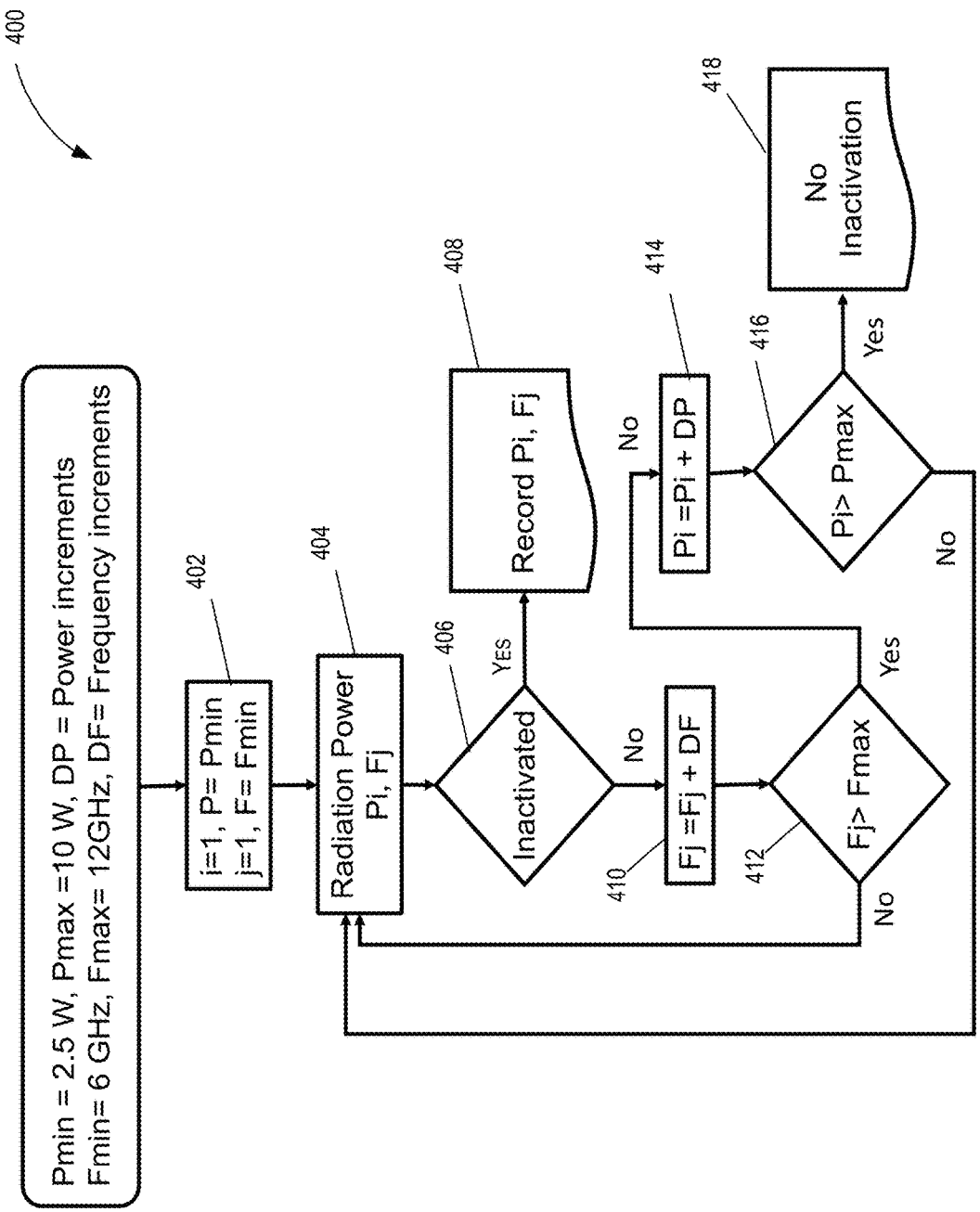
Figure 5:
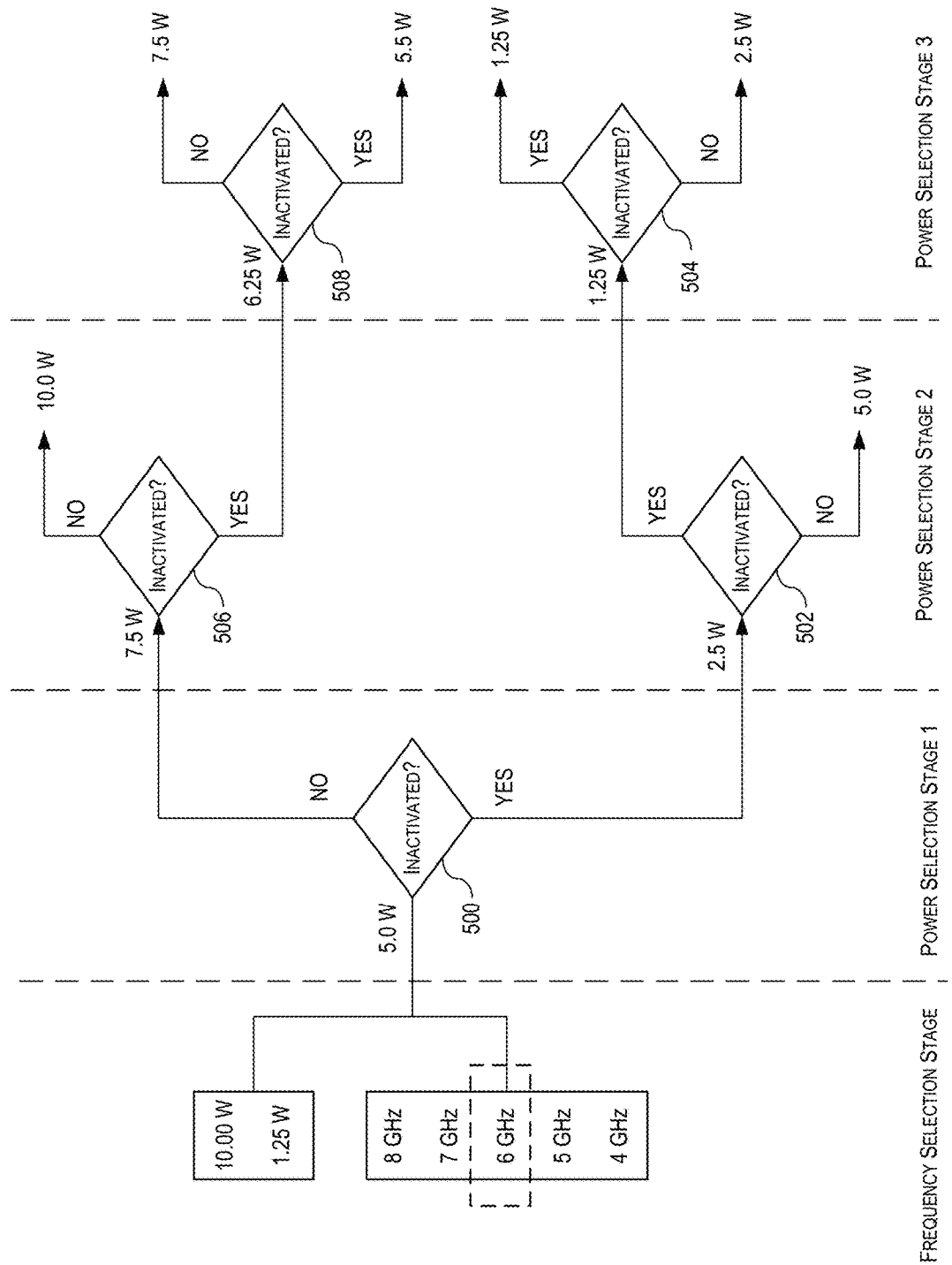

In FIG. 4, a flowchart is shown of an example of an implementation of method 400 for inactivation of viruses with a microwave device 100. The method 400 starts by placing the object 102 with the virus (i.e., a contaminated object) within the cavity 104 of the housing 102 and generating a microwave signal 114 with the microwave signal generator 112. As discussed earlier, the microwave signal 114 is a signal within a band of frequencies and a power level configured to inactivate the virus on the object 102. The microwave signal 114 is received by the field generator 106 and converted to radiating microwave energy 116 that is radiated (also referred to as "irradiated" or "illuminated") into the cavity 104, where the radiated microwave energy 116 is at first at a first frequency from the band of frequencies and a first power level of the microwave signal 114. In this example, the first frequency and the first power level are selected at the microwave signal generator 112 by a user or the controller 122.

The method 400 then determines 406 with the controller 122, if the virus has been inactivated (i.e., destroyed) by the radiated microwave energy 116. In this example, the controller 122 determines whether the virus has been destroyed by utilizing information from the sensor 120. Sensor 120 can be an in-situ Raman Surface Scattering device, or traditionally taking samples for plaque assay. In general, if the virus has been inactivated, the method 400 lowers the power level of the microwave signal 114 (produced by the microwave signal generator 112) to produce a second microwave signal (that has a lower power level than the first microwave signal) and radiates 408 with a fresh active virus and a second microwave energy into the cavity 104 with the field generator 106, where the second microwave energy has a lower power than the first microwave energy.

Specifically, turning to FIG. 4, the method 400 starts by initially setting 402 the microwave signal 114 to a first microwave signal having an initial first frequency (within the band of frequencies) and a first power level and radiating 404 power into the cavity 104 with the first microwave energy at the first frequency and first power level.

The method 400 then determines 406 if the virus has been inactivated by radiating the first microwave energy using, for example, a Raman Surface Scattering method or traditional plaque assays. If the virus has been inactivated, the method 400 records 408 the first frequency and first power level. If, instead, the virus has not been inactivated, the method 400 increments 410 the first frequency to a second frequency and generates a second microwave signal at the second frequency and the first power level.

The method 400 then determines 412 if the second frequency is above a maximum frequency within the band of frequencies and irradiates 404 the cavity 104 with the second microwave signal if the second frequency is less than the maximum frequency. In this example, the maximum frequency corresponds the predetermined maximum frequency capable of destroying the virus.

The method 400 then again determines 406 if the virus has been inactivated after irradiating the cavity 104 with the second microwave energy and records 408 the second frequency and first power level if the virus has been inactivated. If the virus has not been inactivated, the method 400 increments 410 the second frequency to a third frequency, generates a third microwave signal at the third frequency and the first power level, and determines 412 if the third frequency is above the maximum frequency within the band of frequencies. If the third frequency is less than the maximum frequency, the method 400 irradiates 404 the cavity 104 with the third microwave signal.

The method 400 then determines 406 if the virus has been inactivated after irradiating the cavity 104 with the third microwave energy and records 408 the third frequency and first power level if the virus has been inactivated. If the virus has not been inactivated the method 400 increments 414 the first power level to a second power level, determines 416 if the second power level is less than a maximum power level produced by the microwave signal generator, and produces 418 a no inactivation notification if the second power level is more than the maximum power level.

If the second power level is less than the maximum power level, the method 400 then generates a third microwave signal at the second frequency and the second power level and irradiates 404 the cavity 104 with the third microwave signal. The method 400 then determines 406 if the virus has been inactivated after irradiating the cavity 104 with the third microwave energy and records 408 the second frequency and second power level if the virus has been inactivated.

If the virus has not been inactivated, the method 400 then increments 410 the second frequency to a third frequency, generates a fourth microwave signal at the third frequency and the second power level, and determines 412 if the third frequency is above the maximum frequency within the band of frequencies. The method 400 then irradiates 404 the cavity 104 with the fourth microwave signal if the third frequency is less than the maximum frequency.

If the third frequency is greater than the maximum frequency, the method 400 increments 414 the second power level to a third power level, determine 416 if the third power level is less than the maximum power level produced by the microwave signal generator, and produces 418 a no inactivation notification if the third power level is more than the maximum power level.

If the third power level is less than the maximum power level, the method 400 generates a fifth microwave signal at the third frequency and the third power level and irradiates 404 the cavity 104 with the fifth microwave signal if the third power level is less than the maximum power level. The method 400 then determines 406 if the virus has been inactivated after irradiating the cavity with the fifth microwave energy, and records 408 the third frequency and third power level if the virus has been inactivated.

In these examples, the band of frequencies may include frequencies from 6 GHz to 12 GHz. Moreover, irradiating the cavity 104 with a microwave energy includes irradiating the cavity with the microwave energy generated by a helical field generator such as, for example, a helical antenna.

FIG. 5 is a system flow diagram of an example of an implementation of the method 400 in accordance with the present disclosure.

In this example, four stages are shown that include a frequency selection stage, first power selection stage, second power selection stage, and third power selection stage. These stages are all generally controlled by the controller 122 and frequency selection stage is generally performed by selecting the frequency of operation and power levels at the microwave signal generator 112.

In this example, the process starts in the frequency selection stage by selecting an initial operating frequency, for example, 6 GHz and initial power level between, for example, just over 1.25 Watts and 10.00 Watts. In this example, the initial power level is initially 5.0 Watts. As such, the first microwave energy is radiated into the cavity 104 with 5.0 Watts of power and at 6 GHz. The controller 122 with the information from the sensor 120 determines 500 if the virus have been inactivated. If the virus has been inactivated, in the second power selection stage, the power level is dropped down to, for example, 2.5 Watts. The controller 122 with the information from the sensor 120 again determines 502 if the virus have been inactivated. If the virus has not be inactivated, the power level is brought back up to 5.0 Watts to continue destroying the virus. If, instead, the virus has been inactivated, the power level is dropped down to, for example, 1.25 Watts and in the third power selection stage, the controller 122 with the information from the sensor 120 again determines 504 if the virus have been inactivated. If the virus has been inactivated, the power level is dropped down to, for example, 1.25 Watts; however, if the virus has not been inactivated, the power level is increase to the previous 2.5 Watts that previously inactivated the virus.

Returning to decision step 500, if the controller 122 with the information from the sensor 120 instead determines 500 that the virus was not inactivated, the power level is increase to, for example 7.5 Watts and the controller 122 with the information from the sensor 120 determines 506, in the second power selection stage, whether the virus was inactivated. If the virus was not inactivated, the power level is increased to the maximum power of 10.0 Watts. If, instead, the virus was inactivated, the power level is reduced to, for example, 6.25 Watts and the controller 122 with the information from the sensor 120 determines 508, in the third power selection stage, whether the virus was inactivated. If the virus was not inactivated, the power level is increased to, for example, 7.5 Watts and if the virus was inactivated, the power level is decreased to, for example, 5.5 Watts. This process may then be repeated for varying frequencies (selected in the frequency selection stage) and initial power levels.

It will be understood that various aspects or details of the disclosure may be changed without departing from the scope of the disclosure. It is not exhaustive and does not limit the claimed disclosures to the precise form disclosed. Furthermore, the foregoing description is for the purpose of illustration only, and not for the purpose of limitation. Modifications and variations are possible in light of the above description or may be acquired from practicing the disclosure. The claims and their equivalents define the scope of the disclosure. Moreover, although the techniques have been described in language specific to structural features and/or methodological acts, it is to be understood that the appended claims are not necessarily limited to the features or acts described. Rather, the features and acts are described as example implementations of such techniques.

It will also be understood that various aspects or details of the invention may be changed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

The description of the different examples of implementations has been presented for purposes of illustration and description, and is not intended to be exhaustive or limited to the examples in the form disclosed. Many modifications and variations will be apparent to those of ordinary skill in the art. Further, different examples of implementations may provide different features as compared to other desirable examples. The example, or examples, selected are chosen and described in order to best explain the principles of the examples, the practical application, and to enable others of ordinary skill in the art to understand the disclosure for various examples with various modifications as are suited to the particular use contemplated.

I claim:

1. A method for inactivation of viruses with a microwave device, the method comprising:
placing a contaminated object with a virus within a cavity of a housing;
generating a microwave signal with a microwave signal generator, wherein the microwave signal is within a band of frequencies and a power level configured to inactivate the virus, wherein generating the microwave signal includes generating a first microwave signal at a first frequency, within the band of frequencies, and at a first power level;
irradiating the cavity with a microwave energy generated by a field generator in response to receiving the microwave signal, wherein
the cavity is within a near-field of the field generator and
the microwave energy causes a dipole vibration on the virus that causes the virus to fracture;
determining if the virus has been inactivated after irradiating the cavity with the first power level; and
recording the first frequency and first power level if the virus has been inactivated.

2. The method of claim 1, further including:
incrementing the first frequency to a second frequency;
generating a second microwave signal at the second frequency and the first power level;
determining if the second frequency is above a maximum frequency within the band of frequencies; and
irradiated the cavity with the second microwave signal if the second frequency is less than the maximum frequency.

3. The method of claim 2, further including:
determining if the virus has been inactivated after irradiating the cavity with the second microwave signal; and
recording the second frequency and first power level if the virus has been inactivated.

4. The method of claim 2, further including:
incrementing the second frequency to a third frequency;
generating a third microwave signal at the third frequency and the first power level;
determining if the third frequency is above the maximum frequency within the band of frequencies; and
irradiated the cavity with the third microwave signal if the third frequency is less than the maximum frequency.

5. The method of claim 4, further including:
determining if the virus has been inactivated after irradiating the cavity with the third microwave signal; and
recording the third frequency and first power level if the virus has been inactivated.

6. The method of claim 2, further including:
incrementing the first power level to a second power level if the second frequency is greater than the maximum frequency;
determining if the second power level is less than a maximum power level produced by the microwave signal generator; and
producing a no inactivation notification if the second power level is more than the maximum power level.

7. The method of claim 6, further including:
generating a third microwave signal at the second frequency and the second power level; and
irradiated the cavity with the third microwave signal if the second power level is less than the maximum power level.

8. The method of claim 7, further including:
determining if the virus has been inactivated after irradiating the cavity with the third microwave signal; and
recording the second frequency and second power level if the virus has been inactivated.

9. The method of claim 7, further including:
incrementing the second frequency to a third frequency;
generating a fourth microwave signal at the third frequency and the second power level;
determining if the third frequency is above the maximum frequency within the band of frequencies; and irradiated the cavity with the fourth microwave signal if the third frequency is less than the maximum frequency.

10. The method of claim 9, further including:
incrementing the second power level to a third power level if the third frequency is greater than the maximum frequency;
determining if the third power level is less than the maximum power level produced by the microwave signal generator; and
producing a no inactivation notification if the third power level is more than the maximum power level.

11. The method of claim 10, further including:
generating a fifth microwave signal at the third frequency and the third power level; and
irradiated the cavity with the fifth microwave signal if the third power level is less than the maximum power level.

12. The method of claim 11, further including:
determining if the virus has been inactivated after irradiating the cavity with the fifth microwave signal; and
recording the third frequency and third power level if the virus has been inactivated.

13. The method of claim 1, wherein the band of frequencies includes frequencies from 6 GHz to 12 GHz.

14. The method of claim 13, wherein irradiating the cavity with a microwave energy includes irradiating the cavity with the microwave energy generated by a helical field generator.

\* \* \* \* \*